the Patent

United States Patent [19]
Groke et al.

[11] Patent Number: 5,006,551
[45] Date of Patent: Apr. 9, 1991

[54] COMPOSITION FOR DESTROYING MALIGNANT TUMORS

[75] Inventors: Karl Groke, Eggersdorf; Hans Miggitsch, Graz; Horst Musil, Graz; Josef Polzer, Graz, all of Austria

[73] Assignee: Leopold & Co., Chem. Pharm. Fabrik Aktiengesellschaft, Graz, Austria

[21] Appl. No.: 301,035

[22] Filed: Jan. 24, 1989

[30] Foreign Application Priority Data

Feb. 3, 1988 [AT] Austria .................................. 218/88

[51] Int. Cl.$^5$ ...................... A61K 31/34; A61K 31/19
[52] U.S. Cl. ..................................... 514/461; 514/574
[58] Field of Search ............................... 514/461, 574

[56] References Cited

PUBLICATIONS

Leiter et al., Cancer Research, Part 2, vol. 24, No. 3, Apr. 1964, pp. 473–479, 488 and 494 (Entry No. 50778).
K. Schelstraete et al., "The British J. of Radiology", 55(659), 797–804 (1982).
R. Narotzky and W. Bondareff, "The Journal of Cell Biology", 63, 64–70 (1974).
L. V. Bader, A. W. J. Lykke and H. Hinterberger, "Pathology", 9, 353–358 (1977).

Primary Examiner—Jerome D. Goldberg
Attorney, Agent, or Firm—Wenderoth, Lind & Ponack

[57] ABSTRACT

An agent having a destructive effect on malignant tumors and containing as active substances alpha-ketoglutaric acid and 5-hydroxymethylfurfural is described. The agent can be used in cancer therapy both in the form of an infusion solution and as a form for oral or rectal administration or as a douche or ointment.

12 Claims, No Drawings

COMPOSITION FOR DESTROYING MALIGNANT TUMORS

The invention relates to an agent having a destructive effect on malignant tumors, and to a method for the treatment of patients with malignant diseases by prolonged administration of a composition of this type to the patients.

The terms "malignant tumors" and "malignant diseases" are, in general, used interchangeably below and are those tumors or malignant diseases sensitive to treatment with the subject composition.

It is known that a highly significant increase in alpha-kaetoglutaric acid in the blood can be found in patients with malignant tumors. The blood levels mentioned in this connection are 0.30 mg %, while the normal blood level is reported as 0.18 mg %. It has been possible to normalize these elevated blood levels by administration of potassium magnesium aspartate, although only for the duration of the administration, it also having been possible to improve the general condition of the patient (L. Kronberger and E. Fink, "Nachbehandlung operierter Karzinompatienten mit Aspartat" (Postoperative Treatment of Carcinoma Patients with Aspartate), Wissenschaftliche Gesellschaft der Ärzte in der Steiermark, contributions of Dec. 11, 1970, extract from the meeting reports).

On the other hand, K. Schelstraete et al. stated, in The British J. of Radiology, Vol. 55, No. 659 (1982), pages 797 to 804, that malignant tumors show an increased $^{13}NH_3$ uptake which can be determined by positron emission computerized tomography and which diminishes after successful treatment of such tumors. This elevated $^{13}NH_3$ uptake is considerable and, in some malignant tumors, is four to five times as much as in normal tissues. It is also known that there is detectable in a number of malignant tumors a content of biogenic amines such as, for example, dopamine, 5-hydroxytryptamine, epinephrine and norepinephrine, which arise from precursor substances by decarboxylation (R. Narotzky and W. Bondareff, The J. of Cell Biology, 63, 1974, 64–70; L. V. Bader, A. W. J. Lykke and H. Hinterberger, Pathology 9, 1977, 353-358).

The present invention is based on the recognition that the elevated blood level of alpha-ketoglutaric acid might be derived from a disturbance of the citric acid cycle in the cells of the tumor, and this substance, which is injurious to the tumor because of its highly acidic pH, is eliminated from the tumor tissue by means of the ammonia which is present to an increased extent in such tumors, or by means of the amines which are present.

Based on this, it has been found, surprisingly, that when relatively large amounts of alpha-ketoglutaric acid are administered to patients with malignant tumors with the aim of achieving a serum level of this substance which is above that found in such patients, with simultaneous administration of a water-soluble, physiologically tolerated substance which is able, in an enzyme-independent reaction, to bind ammonia and amines with the formation of azomethines, this elimination reaction, which is apparently used for self-protection of the tumor, is defeated, and the consequence is an accumulation of alpha-ketoglutaric acid in the tumor, which results in damage thereto and which may be sufficient to result in complete elimination of the tumor. The substance which has proven to meet the requirement of binding ammonia and amines in an ideal manner is 5-hydroxymethylfurfural.

Accordingly, the present invention relates to a pharmaceutical composition for destroying malignant tumors as defined above, especially in the human body, containing as active substances alpha-ketoglutaric acid and 5-hydroxymethylfurfural. The agent according to the present invention can be both an agent for intravenous administration, preferably an infusion, and an agent for administration by other routes such as, for example, orally or rectally, or, in cases of diseases of body cavities which are open to the outside, also a douche. The use as infusion is very beneficial because this is the way to achieve most reliably a uniform and high blood level of both active substances, which ensures that the destructive effect, according to the invention, on the tumor is displayed in full.

Forms for oral administration, such as capsules and tablets, but also suspensions or solutions, as well as forms for rectal administration, are particularly suitable for the follow-up treatment of patients who have already been treated successfully with the agent according to the invention and who have already been discharged to domiciliary care. However, this by no means exhausts the range of uses of these dosage forms. On the contrary, they are also to be recommended where they allow direct access to be gained to the site of disease, such as is the case, for example, in malignant diseases of the digestive tract, including the colon. The same applies to douches, which may offer advantages for the oral cavity, for example, or to ointment-like preparations, pastes for application or tinctures for the treatment of malignant diseases of the skin. Since alpha-ketoglutaric acid is a strong acid, it is necessary, in order to avoid manifestations of intolerance, to buffer this acid by addition of alkalis to such an extent that the pH of the agent finally reaches a physiologically tolerated range. The requirements for this depend on the dosage form for which the agent is intended. As a rule, it is expedient to adjust the pH to 4–6. An exception is formed by the oral dosage form, in which the pH can be distinctly lower.

However, unacceptable for this adjustment of the pH are all substances, namely ammonia and amines, which would react with the oxo group of 5-hydroxymethylfurfural, since this would result in the effect of this compound, which is to be displayed according to the invention, being lost. In the case of a solid dosage form, it has proven expedient to buffer the ketoglutaric acid by using it directly, in whole or in part, in the form of its monosalts with physiologically tolerated cations.

It has proven advantageous to use the alpha-ketoglutaric acid in the agent according to the invention in an excess by weight compared with the 5-hydroxymethylfurfural.

It is expedient for the ratio by weight between alpha-ketoglutaric acid and 5-hydroxymethylfurfural to be in the range from 2:1 to 12:1, with a ratio by weight of 3:1 to 8:1 being preferred, and one of 6:1 being particularly preferred.

It has furthermore proven beneficial to add to the agent according to the invention a monosaccharide, especially glucose or fructose, since the acidic metabolites thereof support the effect of the alpha-ketoglutaric acid on the malignant tumor and, moreover, there is also a stabilizing effect exerted on the agent. Agents not used for intravenous administration can also, in place of monosaccharides, contain disaccharides, which likewise have a stabilizing effect and, in the case of agents for oral administration, additionally improve the flavor. Finally, it is expedient to incorporate the customary electrolytes needed by the body, with the nature and composition thereof advantageously being chosen such that the desired adjustment of the pH is achieved simultaneously. Ions which are expediently added to the agent according to the invention and which may be mentioned are, as cations, the sodium, potassium, calcium, magnesium and zinc ions and, as anions, the chloride ion and the phosphate ion, with the latter providing a beneficial way of regulating the pH by the choice of primary or secondary phosphate. Of course, it is also possible for phosphate to be introduced in the form of glycerophosphate into the agent. The following composition, for example, has proven very suitable for the formulation of the agent, according to the invention, as an infusion solution:

| | | |
|---|---|---|
| alpha-ketoglutaric acid | 5–20 | g/l |
| 5-hydroxymethylfurfural | 1–3 | g/l |
| glucose | 20–100 | g/l |
| sodium | 60–160 | mmol/l |
| potassium | 15–40 | mmol/l |
| calcium | 3–6 | mmol/l |
| magnesium | 3–6 | mmol/l |
| zinc | 0.03–0.1 | mmol/l |
| chloride ion | 10–25 | mmol/l |
| phosphate ion | 15–30 | mmol/l | and particularly good results were achieved with a composition as follows:

| | | |
|---|---|---|
| alpha-ketoglutaric acid | 6.0–16.0 | g/l |
| 5-hydroxymethylfurfural | 1.0–2.5 | g/l |
| glucose | 20–50 | g/l |
| sodium | 70–160 | mmol/l |
| potassium | 20–40 | mmol/l |
| calcium | 4–6 | mmol/l |
| magnesium | 4–6 | mmol/l |
| zinc | 0.07–0.1 | mmol/l |
| chloride ion | 16–25 | mmol/l |
| phosphate ion | 20–30 | mmol/l |

It is possible to use for oral administration both solid forms such as capsules or tablets and suspensions, which are produced, for example, by forming a suspension of granules, and finally also solutions. As already mentioned, the oral form offers the possibility of directly reaching the disease site in the digestive tract, it being advantageous to modify the formulation of the agent depending on the site of action. Whereas suspensions or solutions are very suitable for treatment of a carcinoma in the stomach, it has proven particularly suitable to use the agent according to the invention in the form of tablets provided with an enteric coating for the treatment of carcinoma of the small intestine. Carcinomas of the colon can be treated not only with infusions but also with a form of the agent according to the invention which is administered in the form of an enema. It is expedient in this case to add to the agent according to the invention, which contains the active substances in solution, a thickening agent such as, for example, methylcellulose, acetylcellulose or polyethylene glycol, in order to avoid, where possible, irritation in the intestine, which might result in ejection of the agent. Finally, carcinomas or metastases which are accessible from the outside can be treated topically, for example by ointment-like preparations or pastes for application, it being expedient to incorporate additives such as, for example, dimethyl sulfoxide which promote the passage of the active substances through the skin.

The agent according to the invention is prepared by converting, in a manner customary in pharmacy, the two active substances into a homogeneous mixture which, in the case where a solution is prepared, can be prepared at the same time as being taken up in a diluent, preferably water. Before, during or after the mixing and taking up in a diluent or mixing with an extender the pH is adjusted to the desired value by addition of alkalis, but not of ammonia or amines. If the agent according to the invention is prepared in the form of an aqueous solution, for example as an infusion solution, the procedure is preferably such that first the alpha-ketoglutaric acid and the other ingredients are dissolved in water, and the pH is preferably adjusted to the range 4–6, before the 5-hydroxymethylfurfural is added. In the case where a solid dosage form is prepared, the active substances and the other additives are mixed in a customary manner and, where appropriate, are granulated together. In this case it is possible and expedient to adjust the desired pH range by use of an appropriate portion, or of the entire amount, of the alpha-ketoglutaric acid in the form of one of its monosalts. Particularly suitable for this is the mono-Na salt, and the use of monosalts of potassium, magnesium or zinc is also very expedient, it also being possible to use mixtures of various monosalts in order to be able to adapt the amount of the individual cations to physiological conditions. It is also preferred in the case of solid preparations initially to mix the monosalt of alpha-ketoglutaric acid, or the mixture thereof with the free acid, with the other ingredients such as electrolytes, extenders and, where appropriate, also sugars, before the 5-hydroxymethylfurfural is added. It has proven beneficial to carry out the preparation of the agent according to the invention, especially when it is a solution, under an inert gas atmosphere, which is intended to help protect the 5-hydroxymethylfurfural from a diminution in activity.

When the agent according to the invention was used in the therapy of patients with malignant tumors of various organs such as lungs, bronchi, breast, bladder, stomach, skin and the like, it was possible with daily administration of the agent according to the invention for a period of only some weeks, for example about 1–2 months, to reach a stage in which the tumor, which had previously been distinctly visible, was no longer detectable in the radiograph, and any metastases which were present were also successfully controlled. This manifest success of treatment was also accompanied by a decided improvement in the general condition of the patients. Remarkably rapid success of treatment was recorded in cases where the cancerous process was still in an early stage.

A particular advantage of the agent according to the invention is also that no harmful or even only unpleasant side effects have been observed. The daily dose in the actual treatment period is, as a rule, about 3–30 g of alpha-ketoglutaric acid and 1–5 g of 5-hydroxymethylfurfural, with the level of the daily dose within this ange depending on the severity of the case but also on general condition of the patient. In cases where the intention is to control the disease site not by generating blood level of the active substances chosen according to the invention but by direct action of the active substances on the disease site, as is possible, for example, with diseases in the gastrointestinal tract by oral or rectal administration, it is possible for the daily dose to be kept somewhat lower as a rule. In these cases it is usually about 3-9 g of alpha-ketoglutaric acid and 0.5-1.5 g of 5-hydroxymethylfurfural.

About the same dose is also indicated when, during the course of an infusion treatment not carried out in hospital, it is intended for a few days on which infusion is impossible to be covered by oral administrations. It is beneficial, after a treatment has been successful, to follow with a follow-up treatment of the patient by administration of the agent according to the invention at a lower daily dose, preferably in a form suitable for oral or rectal administration, in order to stabilize the success which has been achieved. It is advisable in this case to start with the abovementioned dosage for topical use. It is then possible in most cases for the dose to be reduced further, for example even as far as a daily dose of 2.25 g of alphaketoglutaric acid and 0.375 g of 5-hydroxymethylfurfural.

It is important for the success of treatment that the administration of the composition according to the invention takes place each day and that no day is omitted. If the composition according to the invention is, for example, administered parenterally, then days on which parenteral administration is impossible for any reason must be covered by oral administrations or administrations by other routes, for example rectally or topically. Furthermore, the composition according to the invention should act not just for a short period during the day but should act for the maximum possible period of time. This means, in the case where administration is as an infusion, that administration lasts several hours, for example at least 6 hours, and, in the case of oral or rectal administration, that the daily dose is split into divided doses spread throughout the day. On topical treatment, for example in the case of malignant diseases of the skin, it is advisable to protect the applied product from removal, such as, for example, by abrasion, by covering it, such as, for example, by a dressing adhering all round.

If oral administration in the form of tablets or capsules, or else in liquid form, is intended, administration should take place on an empty stomach. Administration with chewed food or immediately before eating carries the risk of inactivation of the composition according to the invention, especially of the 5-hydroxymethylfurfural contained therein, by reactive components in the food. For the same reason, when the colon is treated by enemas, it is recommended that the intestine is previously evacuated and the patient receives parenteral nutrition throughout the medication.

The examples which follow give detailed examples of forms of the agent according to the invention suitable for treatment and of the use thereof in cancer therapy, without intending to restrict the present invention thereto.

EXAMPLE 1

6 g of alpha-ketoglutaric acid are dissolved together with 50 g of glucose at room temperature in 900 ml of water which has been oxygen-depleted by passing gas through, after which the pH of the solution is adjusted to a figure above 4 by addition of 2 g of solid sodium hydroxide. 2 g of 5-hydroxymethylfurfural are introduced and then the resulting solution is made up to 1 l. It is suitable for use as an infusion solution for the treatment of patients with malignant tumors.

EXAMPLE 2

One liter of a solution is prepared from the following substances

| | |
|---|---|
| alpha-ketoglutaric acid | 6.000 g/l |
| 5-hydroxymethylfurfural | 2.000 g/l |
| calcium chloride.2H$_2$O | 0.588 g/l |
| KOH 85% pure | 1.320 g/l |
| MgCl$_2$.6H$_2$O | 0.813 g/l |
| NaOH | 1.200 g/l |
| sodium glycerophosphate.5H$_2$O | 6.122 g/l |
| ZnCl$_2$ | 0.010 g/l |
| glucose | 50.000 g/l | by initially dissolving the alpha-ketoglutaric acid in distilled water, which has previously been oxygen-depleted by passing gas through, at a temperature of about 50° C. Then successively introduced into the resulting solution are NaOH and KOH, the electrolytes and the glucose, with the pH simultaneously being adjusted to above 4. The clear solution obtained in this way is finally stirred while 5-hydroxymethylfurfural is added. This results in a clear pale yellow solution which contains per liter 6 g of alpha-ketoglutaric acid, 2 g of 5-hydroxymethylfurfural, 50 g of glucose and electrolytes in the following molar concentrations:

| | |
|---|---|
| Na | 70.00 mmol/l |
| K | 20.00 mmol/l |
| Ca | 4.00 mmol/l |
| Mg | 4.00 mmol/l |
| Zn | 0.07 mmol/l |
| chloride | 16.00 mmol/l |
| phosphate | 20.00 mmol/l |

The pH of the solution is 4.90, and the calculated osmolality of the solution is 490 mosmol/kg H$_2$O. It is dispensed into bottles of ½ liter capacity for administration as an infusion solution.

EXAMPLE 3

1 liter of a solution is prepared as described in Example 2 from

| | |
|---|---|
| alpha-ketoglutaric acid | 16.000 g/l |
| 5-hydroxymethylfurfural | 2.000 g/l |
| NaOH | 4.000 g/l |
| KOH 85% pure | 2.640 g/l |
| sodium glycerophosphate.5H$_2$O | 9.184 g/l |
| MgCl$_2$.6H$_2$O | 1.220 g/l |
| CaCl$_2$.2H$_2$O | 0.883 g/l |
| ZnCl$_2$ | 0.014 g/l |
| glucose | 20.000 g/l | and contains, besides 16 g of alpha-ketoglutaric acid, 2 g of 5-hydroxymethylfurfural and 20 g of glucose the electrolytes in the following molar concentration:

| | |
|---|---|
| sodium | 160 mmol/l |
| potassium | 40 mmol/l |
| calcium | 6 mmol/l |
| magnesium | 6 mmol/l |
| zinc | 0.1 mmol/l |
| chloride | 24.2 mmol/l |
| phosphate | 30 mmol/l |

The pH of the solution is 4.1, and the calculated osmolality is about 530 mosmol/kg $H_2O$. The solution is dispensed into infusion bottles of ½ liter capacity.

EXAMPLE 4

1 liter of a solution is prepared as described in Example 2 from

| | |
|---|---|
| alpha-ketoglugaric acid | 12.000 g/l |
| 5-hydroxymethylfurfural | 2.000 g/l |
| $CaCl_2.2H_2O$ | 0.883 g/l |
| KOH 85% pure | 1.980 g/l |
| $MgCl_2.6H_2O$ | 1.220 g/l |
| NaOH | 2.800 g/l |
| Na2 glycerophosphate.$5H_2O$ | 9.184 g/l |
| $ZnCl_2$ | 0.019 g/l |
| glucose | 20.000 g/l | and contains the two active substances in the ratio 6:1. Also present are electrolytes in the following molar concentration:

| | |
|---|---|
| Na | 130.0 mmol/l |
| K | 30.0 mmol/l |
| Ca | 6.0 mmol/l |
| Mg | 6.0 mmol/l |
| Zn | 0.1 mmol/l |
| chloride | 24.2 mmol/l |
| phosphate | 20.0 mmol/l |

The pH of the solution is 4.68. It is dispensed into infusion bottles of ½ liter capacity.

EXAMPLE 5

345.12 g of mono-Na alpha-ketoglutarate, 0.8 g of zinc oxide and 1204 g of powdered sugar are mixed dry in a planetary mixer and screened through a screen of mesh size 0.7 mm. The material obtained in this way is returned to the mixer and, with the mixer running, 100 g of distilled water are added and mixing is continued until agglomerates form. After the product has been dried at 50° C. it is granulated through a screen of mesh size 1.25 mm and is mixed in a planetary mixer with 50.0 g of 5-hydroxymethylfurfural. The pH is about 3. 1600 g of a composition which can be used as instant granules are obtained. It is dispensed into one-portion sachets each containing 4 g. This one-portion sachet contains 0.75 g of alpha-ketoglutaric acid and 0.125 g of 5-hydroxymethylfurfural.

EXAMPLE 6

1.2 g of alpha-ketoglutaric acid in the form of the mono-Na salt are mixed with 0.2 g of 5-hydroxymethylfurfural, 3.6 g of sucrose and 0.002 g of zinc oxide and dissolved by addition of water to a volume of 20 ml. This solution is used to prepare a drinkable ampoule. The products of Examples 5 and 6 are intended for oral administration, especially for the treatment of cases with carcinoma of the upper digestive organs such as the stomach.

EXAMPLE 7

The same substances as in Example 6, but with the difference that customary lubricants and disintegrants are used in place of the sucrose, are converted into tablets and then provided with an enteric coating. They can be used to treat tumors of the small intestine. Example 8:

15 g of methylcellulose, which is in the form of a liquid mucilage, are mixed with 6 g of alpha-ketoglutaric acid, 1.2 g of NaOH, 0.726 g of 85% pure KOH, 16 g of $NaH_2PO_4.2H_2O$ and 6 g of $Na_2HPO_4.12H_2O$, and finally with 1 g of 5-hydroxymethylfurfural. The resulting solution has a viscosity of 20–50 cp and a pH of about 6 and is made up to 1 l. It can be administered in portions of about ¼ liter as an enema and is preferably used for the treatment of colon carcinomas, in which case the daily dose is 2 enemas.

EXAMPLE 9

A 33-year old male patient with an inoperable bronchial carcinoma which was the size of a chicken's egg and had an unfavorable prognosis received an infusion of ½ liter of the solution of Example 2 each day for 30 days, corresponding to a daily dose of 3 g of alpha-ketoglutaric acid and of 1 g of 5-hydroxymethylfurfural. After the 30 days had elapsed the tumor was no longer radiologically detectable. The mood of the patient, who had previously been depressed, became positive again, and he developed a keen appetite.

EXAMPLE 10

A male patient of 78 who suffered from recurrent bladder carcinoma with pulmonary metastases received an infusion of ½ liter of the solution from Example 2 each day for 30 days. After this, neither the bladder tumor nor the pulmonary metastases were radiologically detectable.

EXAMPLE 11

A 70-year old female patient underwent surgical removal of an ulcerating carcinoma of the breast with multiple local metastases. Because metastases developed again immediately after the operation, she was given an infusion of ½ liter of the solution of Example 2 each day. This infusion treatment had to be discontinued after 7 days because of venous intolerance. Because a metastasis developed in the form of a hard node in the healed operation area shortly after the site of operation had healed, the infusion treatment was resumed taking the utmost care in the administration. After 7 infusions each of ½ liter of the solution of Example 2, the hard node had softened and, after a further 7 infusions, the region of the original hard node was normal. The infusion treatment was continued for 6 days to be safe.

EXAMPLE 12

An 87-year old patient who suffered from a primary carcinoma of the prostate with pulmonary metastases, which frequently caused hemoptysis and breathing difficulties, received ½ liter of the solution of Example 2 each day for 16 days. At the checkup which was then carried out, the prostate had returned to the normal consistency and the circular foci in the lungs were no longer visible on the X-ray screen. The patient no longer had the urge to cough and stated that he was able to breath easily again.

EXAMPLE 13

The findings at a checkup on a patient with Hodgkin's disease (lymphogranulomatosis) in stage IV with an unfavorable prognosis were, after 15 infusions each of ½ liter of the solution of Example 2, as follows: of the initially swollen lymph nodes on the neck, armpits and groin, the swelling of the axillary lymph nodes had reduced while the other lymph nodes were still swollen, but the physician stated that the overall condition of the patient had improved.

EXAMPLE 14

A patient who was found at a follow-up gastroscopic examination after a gastric ulcer to have a distinct precancerosis and who was advised to have an extensive partial gastrectomy received one portion of the instant granules of Example 5, which were suspended in water, 3×each day for 4 days, with the patient executing a slow roll. At the follow-up examination carried out on day 4, at which samples of the gastric mucosa were once again taken, it was no longer possible to detect any malignancy in the tissue which underwent cytological investigation. The patient then continued the treatment with the same daily dose of the instant granules of Example 5 for a further 6 weeks. At the subsequent second follow-up examination it was again impossible to detect any malignancy in the samples of the gastric mucosa which were taken and underwent cytological testing.

EXAMPLE 15

A 79-year old female patient with a carcinoma of the breast which had undergone palliative surgery showed, after the operation had taken place, lymph node swelling which indicated the development of distant metastases. The general condition was poor and there was loss of weight but infusion therapy using the solution of Example 2 at a daily dose of 1 g of 5-hydroxymethylfurfural and 3 g of alpha-ketoglutaric acid was initiated. A distinct improvement was noted after the 6th infusion. Then, after administration of a total of 14 infusions, there was a changeover to subsequent oral treatment in which the patient received 3 portions of the instant granules of Example 5 each day, that is to say 2.25 g of alpha-glutaric acid and 0.375 g of 5-hydroxymethylfurfural each day. This oral therapy was continued for 6 months. At a subsequent checkup, the lymph node swelling was no longer palpable, nor was it any longer detectable in the radiograph. The patient noted an increase in weight and showed a considerably improved general condition.

In principle, it is also possible to treat in the same way all other malignant tumors associated with an elevation of the serum alpha-ketoglutaric acid.

We claim:

1. A method for treating patients with malignant diseases sensitive to treatment with the composition below, which comprises administration to said patients over a period of several weeks, of a cytostatically effective amount of a composition by the parenteral, oral, rectal or topical route, which composition contains alpha-ketoglutaric acid and 5-hydroxymethylfurfural, in a daily dose of 2.25-30 g of alpha-ketoglutaric acid and 0.375-5 g of 5-hydroxymethylfurfural.

2. The method as claimed in claim 1, in which the daily dose is 3-30 g of alpha-ketoglutaric acid and 1-5 g of 5-hydroxymethlfurfural, and which daily dose is administered to said patients in a period lasting several hours or in a single dose distributed over the day.

3. The method as claimed in claim 2, in which several weeks of administration to said patients of 3-30 g of alpha-ketoglutaric acid and 1-5 g 5-hydroxymethylfurfural each day are followed by a treatment period in which 2.25-9 g of alpha-ketoglutaric acid and 0.375 to 1.5 g of 5-hydroxymethylfurfural are administered to said patients each day.

4. The method according to claim 1 wherein said malignant disease is bronchial carcinoma, bladder carcinoma, breast carcinoma, prostate carcinoma, Hodgkin's disease or precancerosis of the gastric mucosa.

5. A method for treatment of malignant diseases sensitive to treatment with the combination below in a human patient which comprises administering to said patient an effective amount of the combination of alpha-ketoglutaric acid and 5-hydroxymethylfurfural in amounts sufficient to cause accumulation of alpha-ketoglutaric and bind ammonia and amines with the formation of azomethines in the vicinity of said malignancy and said alpha-ketoglutaric acid being present in an amount of at least two times by weight compared with the 5-hydroxymethyl-furfural.

6. A pharmaceutical composition for treatment of malignant diseases sensitive to treatment with the combination below, in the human body, comprising as active substances, alpha-ketoglutaric acid and 5-hydroxymethylfurfural, said alpha-ketoglutaric acid being present in an amount of at least two times by weight compared with the 5-hydroxymethylfurfural and the amount of said alpha-ketoglutaric acid and 5-hydroxymethylfurfural being effective to cause accumulation of alpha-ketoglutaric acid bind ammonia and amines with the formation of azomethines in the vicinity of said malignancy.

7. The composition as claimed in claim 6, in which the ratio by weight of alpha-ketoglutaric acid to 5-hydroxymethylfurfural is 2:1 to 12:1.

8. The composition as claimed in claim 7, in which the ratio by weight is 3:1 to 8:1.

9. The composition as claimed in claim 7, which additionally contains glucose or fructose.

10. The composition as claimed in claim 7, which additionally contains electrolytes selected from the group consisting of sodium, potassium, calcium, magnesium and zinc ions, together with chloride ion and phosphate ion as anions.

11. The composition as claimed in claim 7, which is an aqueous infusion solution with the following composition:

| | |
|---|---|
| alpha-ketoglutaric acid | 5-20 g/l |
| 5-hydroxymethylfurfural | 1-3 g/l |
| glucose | 20-100 g/l |
| sodium | 60-160 mmol/l |
| potassium | 15-40 mmol/l |
| calcium | 3-6 mmol/l |
| magnesium | 3-6 mmol/l |
| zinc | 0.03-0.1 mmol/l |
| chloride ion | 10-25 mmol/l |
| phosphate ion | 15-30 mmol/l |

12. The composition as claimed in claim 7, which is suitable for oral administration and is solid or liquid, in which the entire amount of alpha-ketoglutaric acid or at least a part thereof is present as the monosodium salt or monopotassium salt.

* * * * *